United States Patent
Kravis et al.

(10) Patent No.: US 9,801,593 B2
(45) Date of Patent: Oct. 31, 2017

(54) INTRAORAL X-RAY IMAGING SENSOR AND READOUT

(71) Applicant: Dental Imaging Technologies Corporation, Hatfield, PA (US)

(72) Inventors: Scott David Kravis, Lambertville, NJ (US); Bradley S. Carlson, Doylestown, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 136 days.

(21) Appl. No.: 14/968,310

(22) Filed: Dec. 14, 2015

(65) Prior Publication Data

US 2017/0164914 A1    Jun. 15, 2017

(51) Int. Cl.
*A61B 6/14* (2006.01)
*A61B 6/00* (2006.01)

(52) U.S. Cl.
CPC ............ *A61B 6/145* (2013.01); *A61B 6/4233* (2013.01)

(58) Field of Classification Search
CPC  G01T 1/247; G01T 1/208; G01T 1/17; G01T 1/20; A61B 6/425; A61B 1/00; A61B 6/4233; A61B 6/032
USPC ...................... 378/98.8, 19, 38, 191; 250/366
See application file for complete search history.

(56) References Cited

U.S. PATENT DOCUMENTS

| | | | |
|---|---|---|---|
| 5,510,623 A | 4/1996 | Sayag et al. | |
| 7,462,807 B2 | 12/2008 | Caupain et al. | |
| 7,605,376 B2 | 10/2009 | Liu | |
| 7,623,172 B2 | 11/2009 | Wada et al. | |
| 7,655,918 B2 | 2/2010 | Liu et al. | |
| 7,916,200 B2 | 3/2011 | Ligozat et al. | |
| 8,334,491 B2 | 12/2012 | Bogaerts et al. | |
| 8,643,750 B2 | 2/2014 | Mo et al. | |
| 9,408,581 B2 * | 8/2016 | Hyde ..................... | A61B 6/145 |
| 2006/0237625 A1 | 10/2006 | Caupain et al. | |
| 2008/0244228 A1 | 10/2008 | Overdick et al. | |
| 2009/0033777 A1 | 2/2009 | Ligozat et al. | |
| 2010/0141820 A1 | 6/2010 | Chenebaux et al. | |
| 2010/0295982 A1 | 11/2010 | Kyushima et al. | |

(Continued)

FOREIGN PATENT DOCUMENTS

EP    1255401 A1    11/2002

OTHER PUBLICATIONS

International Search Report and Written Opinion for Application No. PCT/US2016/065635 dated Apr. 4, 2017 (14 pages).

(Continued)

*Primary Examiner* — Don Wong
(74) *Attorney, Agent, or Firm* — Michael Best & Friedrich LLP

(57) ABSTRACT

Devices, methods, and systems including an intraoral x-ray imaging sensor. The intraoral x-ray imaging sensor having a substrate having an imaging area and a non-imaging area, a plurality of readout amplifiers located in the non-imaging area of the substrate, an array of pixels located on the imaging area of the substrate and arranged as a plurality of rows and columns, and pixel selector circuitry diagonally arranged in the imaging area of the substrate. Each pixel of the array of pixels is selectively coupled to one or more of the plurality of readout amplifiers.

23 Claims, 10 Drawing Sheets

(56) References Cited

U.S. PATENT DOCUMENTS

2015/0189208 A1 7/2015 Guerrini et al.

OTHER PUBLICATIONS

"CMOS Digital Intra-Oral Sensor for X-ray Radiography", Xinqiao (Chiao) Liu et al., Fairchild Imaging Inc., 1801 McCarthy Blvd, Milpitas, CA 95035, USA, Medical Imaging 2011: Physics of Medical Imaging, edited by Norbert J. Pelc et al., Proc. of SPIE vol. 7961, 79614M.

* cited by examiner

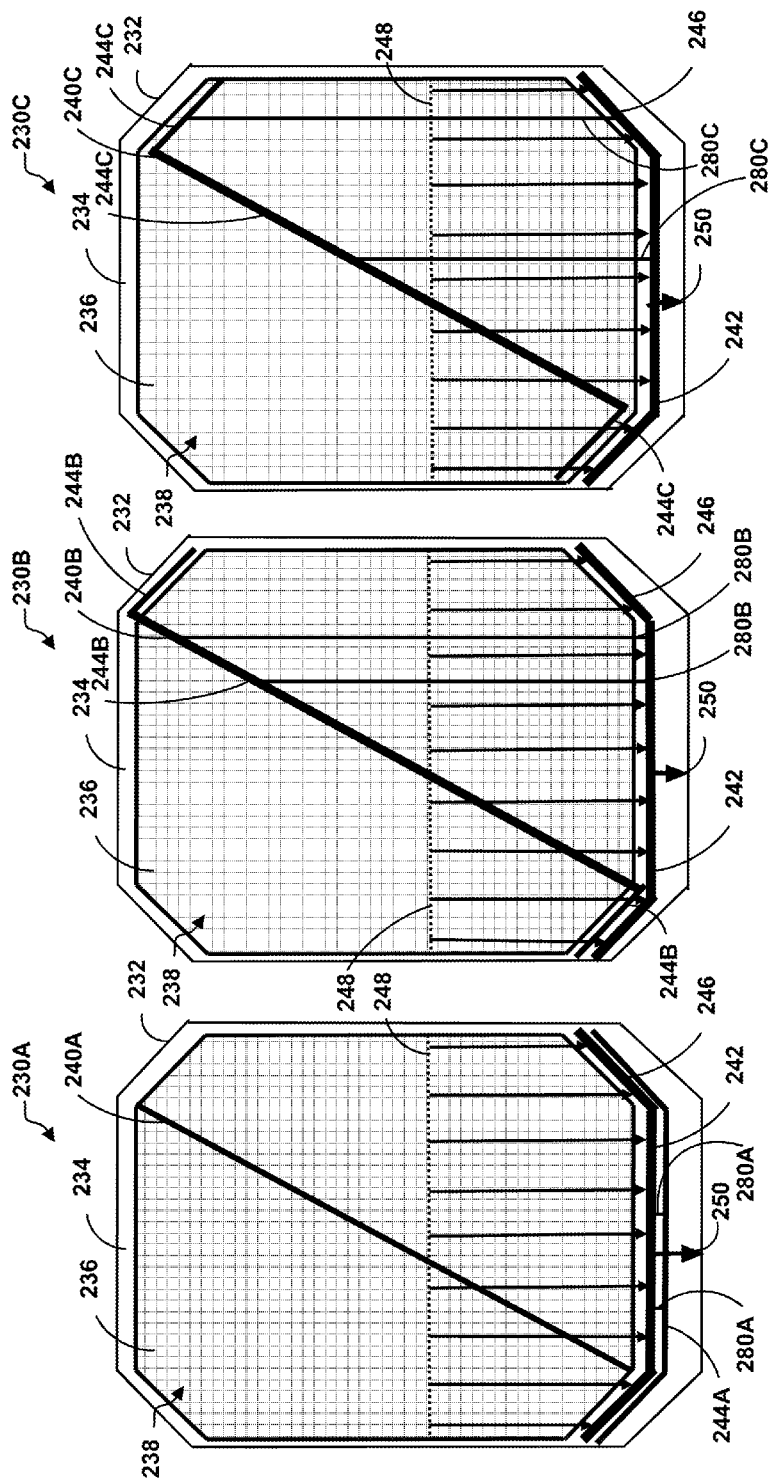

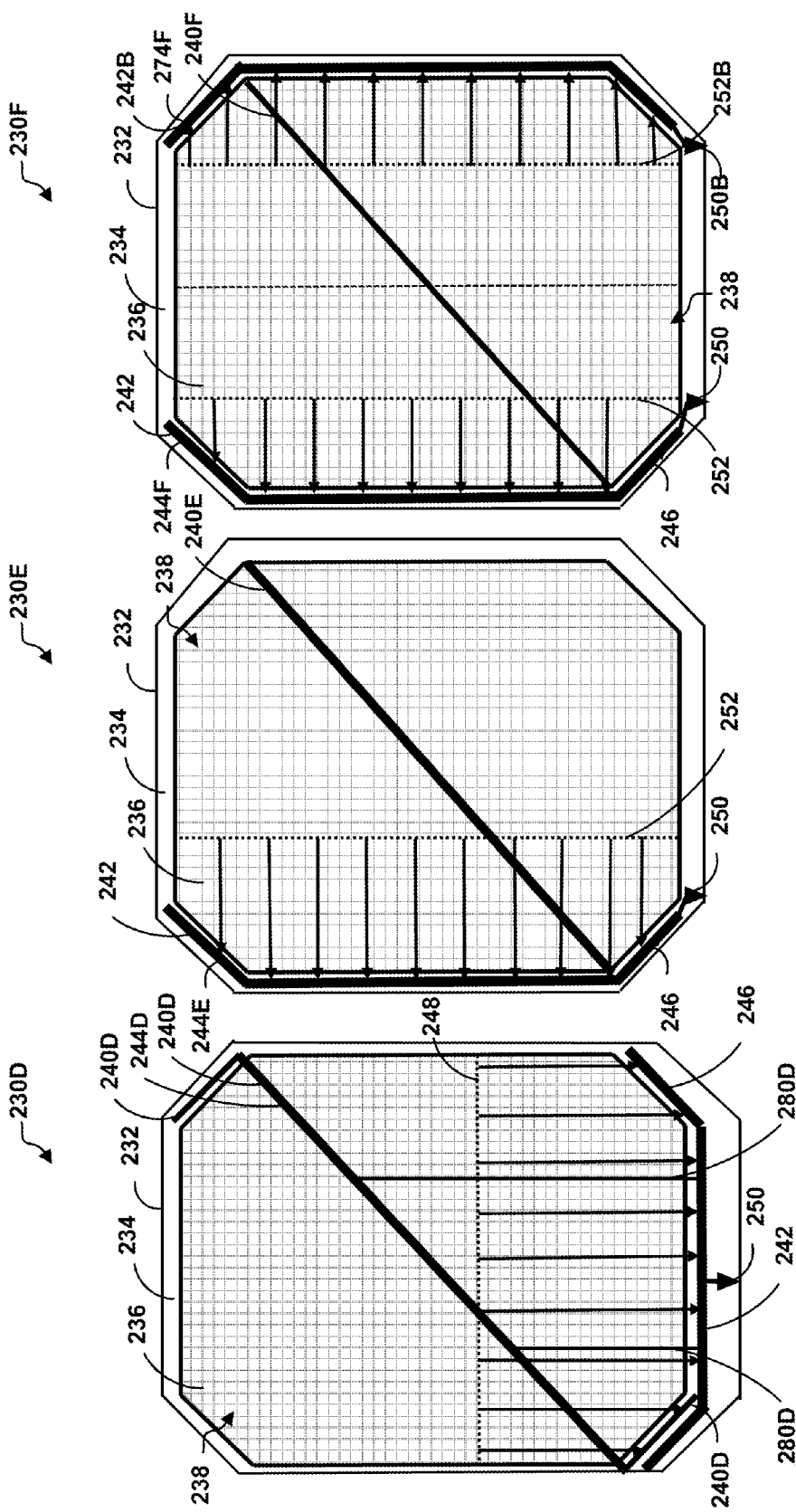

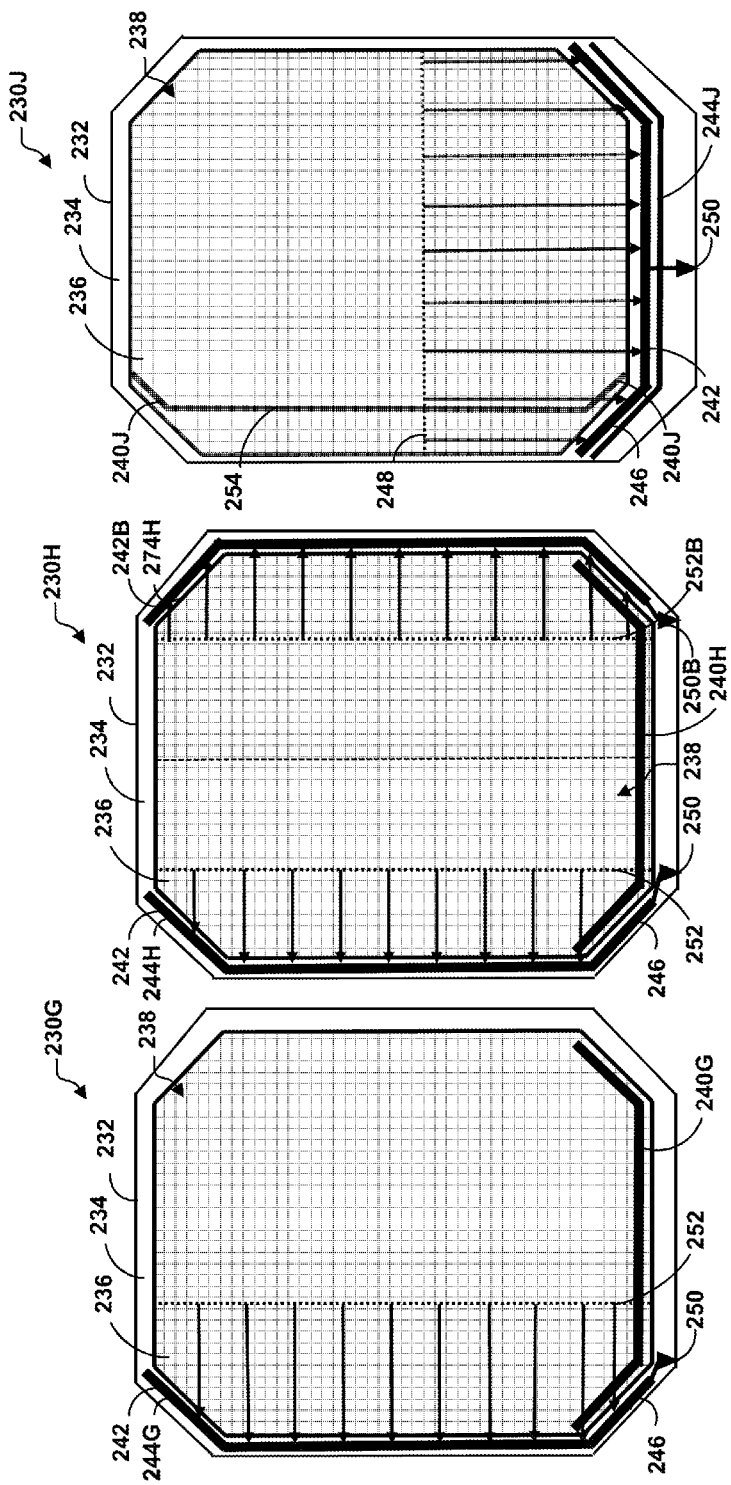

INTRAORAL X-RAY IMAGING SENSOR AND READOUT

FIELD

Embodiments of the invention relate to intraoral x-ray systems, intraoral x-ray sensors, and methods for operating intraoral x-ray imaging sensors.

BACKGROUND

When acquiring intraoral x-ray images, an intraoral x-ray sensor is placed in a patient's mouth by an x-ray technician or operator. X-rays are directed to the patient's mouth and an x-ray image is recorded with the intraoral x-ray sensor. The intraoral x-ray sensor may include features to increase the comfort level of the patient—e.g., rounded corners.

SUMMARY

In one embodiment, the invention provides an intraoral x-ray imaging sensor. The intraoral x-ray imaging sensor comprises a substrate having an imaging area and a non-imaging area, a plurality of readout amplifiers located in the non-imaging area of the substrate, an array of pixels located on the imaging area of the substrate and arranged as a plurality of rows and columns, and a pixel selector circuitry diagonally arranged in the imaging area of the substrate. In this embodiment, each pixel of the array of pixels is selectively coupled to one or more of the plurality of readout amplifiers.

In another embodiment the invention provides a method of capturing an x-ray image with an intraoral x-ray imaging sensor. The method includes initiating a readout sequence by conveying a signal to a pixel selector circuitry, selectively coupling each pixel in a selected row or selected column of an array of pixels located in the imaging area to one or more of a plurality of readout amplifiers, receiving, at the one or more of a plurality of readout amplifiers, a signal from at least one pixel in the selected row or selected column, and outputting a signal from the one or more of the plurality of readout amplifiers based on the signal from the at least one pixel until the readout sequence for capturing the x-ray image is completed. In one embodiment, the pixel selector circuitry is diagonally arranged in an imaging area of a substrate of the intraoral x-ray imaging sensor.

In yet another embodiment the invention provides a dental x-ray system. The system including an intraoral x-ray imaging sensor and a dental image generation device. The intraoral x-ray imaging sensor having a substrate having an imaging area and a non-imaging area, a plurality of readout amplifiers located in the non-imaging area of the substrate, an array of pixels located in the imaging area of the substrate and arranged as a plurality of rows and columns, and each pixel of the array of pixels is selectively coupled to one or more of the plurality of readout amplifiers, and a pixel selector circuitry diagonally arranged in the imaging area of the substrate. The dental image generation device having memory and one or more processors. The one or more processors of the dental image generation device are configured to receive signals from the intraoral x-ray imaging sensor, interpolate the pixels that correspond to the pixel selector circuitry with pixels that are near the pixel selector circuitry, generate a dental image that includes the interpolated pixels, and store the dental image in the memory.

In another embodiment the invention provides a method for operating a dental x-ray system. The method includes receiving signals from an intraoral x-ray imaging sensor, interpolating pixels that correspond to the pixel selector circuitry with pixels that are near the pixel select circuitry, and generating a dental image that includes the interpolated pixels.

In yet another embodiment the invention provides an intraoral x-ray imaging sensor. The intraoral x-ray imaging sensor having a substrate having an imaging area and a non-imaging area, a plurality of readout amplifiers located in the non-imaging area of the substrate, an array of pixels located on the imaging area of the substrate and arranged as a plurality of rows and columns, wherein each pixel of the array of pixels is selectively coupled to one or more of the plurality of readout amplifiers, and a pixel selector circuitry diagonally arranged in the non-imaging area of the substrate.

Other aspects of the invention will become apparent by consideration of the detailed description and accompanying drawings.

BRIEF DESCRIPTION OF THE DRAWINGS

FIGS. 2-10 are schematic views of different examples of intraoral x-ray imaging sensors including a non-imaging area and an imaging area with a diagonally arranged pixel selector circuitry for use in the dental x-ray system of FIG. 1.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
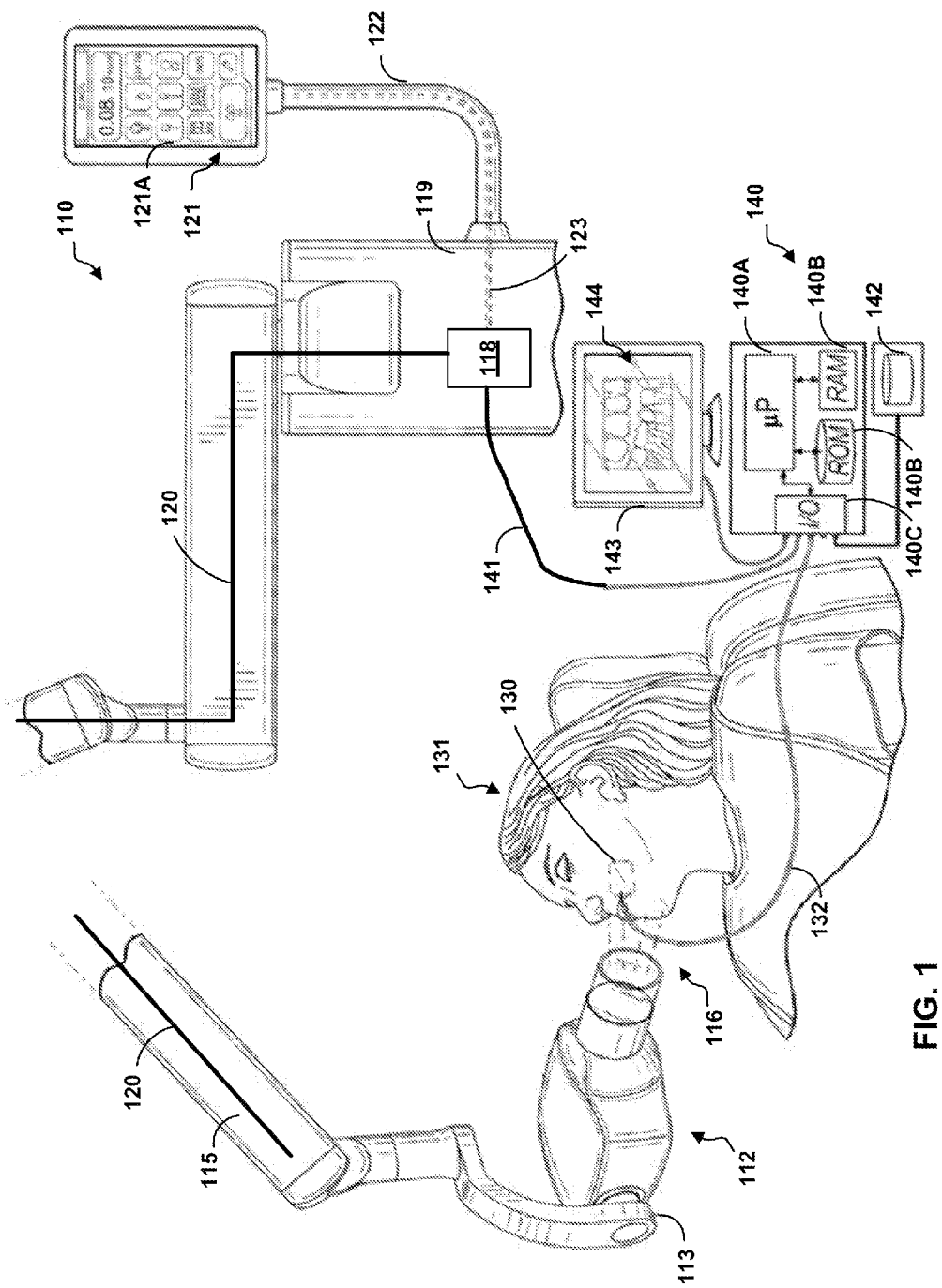
FIG. 1 is a schematic view of a dental x-ray system.

FIG. 1 is a schematic view illustrating a dental x-ray system 110. The system 110 includes an x-ray source 112. In the illustrated embodiment, the source 112 is located at an end 113 of a mechanical arm 115. When activated, the x-ray source 112 generates an x-ray stream 116 that has a generally circular cross-section. (Although x-rays are generally invisible, a representation of a stream is illustrated to facilitate understanding of the invention.) In some applications, a collimator (not shown) is used to reduce the size of the stream 116 and generate a smaller x-ray stream having a different shaped cross-section (e.g., rectangular, or some other shape). The collimator can also be used to change the shape of the stream and/or collimating the stream on a particular anatomical site of interest.

The system 110 also includes a controller 118. As illustrated in FIG. 1, the controller 118 can be included inside a housing 119 located at the base or shoulder of the arm 115. In this configuration, the controller 118 is connected to the x-ray source 112 using a connection 120 (e.g., a wire, cable, or the like) that runs from the x-ray source 112 to the controller 118 through the arm 115. In some embodiments, the controller 118 may be located within the housing of the x-ray source 112. In some other embodiments, the connection 120 between the x-ray source 112 and the controller 118 includes a wireless connection—for example, without limitation, Bluetooth, Wi-Fi, or any other suitable wireless connection protocol.

The controller 118 and the x-ray source 112 are collectively referred to herein as an x-ray unit. The controller 118 monitors and controls operation of the x-ray source 112. In some examples, the controller 118 includes a processing unit, which can be, for example, a microprocessor or an application-specific integrated circuit ("ASIC"). The controller 118 also includes one or more non-transitory memory modules, for example, a random access memory ("RAM") module and a read-only memory ("ROM") module. The memory modules can store software and/or associated data for monitoring and controlling the x-ray source 112 and/or other aspects of the system 110.

In addition, the controller 118 includes an input/output interface. The input/output interface communicates with systems and devices external to the controller 118, including the x-ray source 112 and a user interface 121. In some embodiments, the controller 118 may also include a user interface module. In these embodiments, the user interface module may be configured to communicate with the user interface 121 (e.g., over a universal serial bus ("USB") cable). For example, the user interface module of the controller 118 can be configured to generate screens for display on the user interface 121. In addition, the user interface module of the controller 118 can be configured to receive inputs from an operator received through the user interface 121. Accordingly, in some embodiments, the user interface module communicates with the user interface 121 rather than the input/output interface.

As illustrated in FIG. 1, in some embodiments, the user interface 121 includes a touchscreen 121A. However, it should be understood that the user interface 121 can include different types of input and output devices and combinations of the same (e.g., a keyboard, tactile buttons, a joystick, a mouse, a non-touch screen display, etc.). The user interface 121 is located external to x-ray source 112 and the controller 118. In some embodiments, the user interface 121 is contained within the housing 119 located at the base or shoulder of the arm 115. In other embodiments, as illustrated in FIG. 1, the user interface 121 can be mounted on a separate extension 122 connected to the arm 115. In some embodiments, the extension 122 is flexible to allow an operator to change the position of the user interface 121. It should be understood that the user interface 121 can also be located outside of the room where the x-ray source is located to allow the operator to avoid radiation exposure. In other embodiments, the user interface 121 can be located in the same room as the x-ray source but protected from radiation exposure using shielding material.

Regardless of where the user interface 121 is positioned, the user interface 121 is connected to the controller 118 (i.e., through the input/output interface) over a connection 123. In some embodiments, the connection 123 (e.g., a wire or a cable) between the controller 118 and the user interface 121 can be positioned external to the arm 115. However, in other embodiments, the connection 123 can be accomplished by routing a wire from the controller 118 to the user interface 121 internal to the housing 119. Also, in some embodiments, the user interface 121 can communicate with the controller 118 using a wireless connection, a wired connection, or a combination of wired and wireless connections. In response to inputs from an operator, the user interface 121 is configured to manually control the x-ray source 112. In particular, an operator can use the user interface 121 to manually set one or more adjustable exposure parameters of the x-ray source 112. The exposure parameters can include a voltage (e.g., in kilovolts ("kV")), a current (e.g., in milliamps ("mA")), and an exposure time (e.g., in milliseconds ("ms")). The controller 118 receives the parameters and uses the parameters (in combination with the software and data stored in the memory modules of the controller 118) to monitor and control the x-ray source 112.

In some embodiments, the x-ray source 112 is activated in response to a signal received from a remote switch (not shown). The remote switch communicates with the controller 118, which, in turn, starts and/or stops the x-ray stream 116. The remote switch can communicate with the controller 118 over a wired or wireless connection (e.g., through the input/output interface). An operator can start and stop the x-ray source 112 using the remote switch from a different room or location than the x-ray source 112 to avoid radiation exposure.

As illustrated in FIG. 1, the x-ray source 112 is positioned (e.g., manually by an operator (not shown)) so that the x-ray stream 116 is directed toward an intraoral x-ray imaging sensor 130 located in the mouth of a patient 131. The intraoral x-ray imaging sensor 130 can include a digital detector or sensor. In the example of FIG. 1, a wire, cable, or similar connection 132 connects the intraoral x-ray imaging sensor 130 to an image processing unit 140. The connection 132 between the intraoral x-ray imaging sensor 130 and the image processing unit 140 can alternatively be a wireless connection, a fiber-optic connection, or other connection suitable for transmitting data between the devices. In some embodiments, the connection 132 also provides an electrical return path that allows electrical signals to be provided to and/or received from the intraoral x-ray imaging sensor 130 and or a holder for the intraoral x-ray imaging sensor 130. The electrical signals can be used to identify a type or placement of the intraoral x-ray imaging sensor 130 that indicates what image in a sequence of images is being acquired. In other embodiments, a separate connection (e.g., a separate wire) is used to provide the electrical signals. Although, the x-ray source 112 is illustrated as a wall-mounted unit, it is understood that the x-source 112 may also be a handheld portable unit (e.g., the NOMAD handhold x-ray system).

The image processing unit 140 includes a processing unit 140A, which can be, for example, a microprocessor or an ASIC. The image processing unit 140 also includes one or more non-transitory memory modules 140B, e.g., a RAM module and a ROM module. The memory modules 140B stores software and data for processing image data collected by the intraoral x-ray imaging sensor 130 (e.g., to mitigate an occlusion in a dental image by generating an image with interpolated pixels from proximate pixels). The memory modules 140B also stores image data and/or associated metadata for the image data (e.g., a log of exposure times, etc.). In addition, as described in more detail below, the memory modules 140B stores software and data for generating an image with interpolated pixels.

In some embodiments, the software stored on the memory modules 140B is the DEXIS Imaging Suite provided by Dental Imaging Technology Corp. For example, the software stored on the memory modules 140B may include instructions stored on a non-transitory computer-readable medium, that when executed, cause the processor to interpolate the pixels that correspond to the pixel selector circuitry with nearby pixels, and generate a dental image 144 that includes the interpolated pixels. Additionally, in some embodiments, the non-transitory computer-readable medium may further store instructions, that when executed, cause the processor to display the dental image 144 on display devices 143.

As illustrated in FIG. 1, the image processing unit 140 also includes an input/output interface 140C. The input/output interface 140C communicates with systems and devices external to the image processing unit 140, including, for example, the intraoral x-ray imaging sensor 130 and the controller 118. For example, the image processing unit 140 can communicate with the controller 118 over a connection 141. The connection 141 can include a wire or a cable. In other embodiments, the connection 141 can include a wireless connection. Although the connection 141 illustrated in FIG. 1 is shown as being external to the housing 119, it should be understood that the connection 141 can be routed through one or more components of the system 110 (e.g., the housing 119, the arm 115, or any other suitable component).

In some embodiments, the input/output interface 140C also communicates with one or more an external data storage devices 142 that store images acquired using the system 110, which can include cloud storage. As also illustrated in FIG. 1, the input/output interface 140C can also communicate with one or more display devices 143. The display device(s) 143 can be used to display images acquired through use of the system 110. In particular, during operation of the system 110, image data is captured by the intraoral x-ray imaging sensor 130, the data is processed by the image processing unit 140, and the processed data is sent to a display device 143 where it can be viewed as an image 144. (Image 144 is drawn more distinctly than an x-ray image would typically appear.) In some embodiments, the display device(s) 143 include a touchscreen that receives input from an operator. The image processing unit 140 can also include one or more additional peripheral devices for receiving input from an operator (e.g., a keyboard, mouse, joystick, etc.).

It should be understood that the intraoral x-ray imaging sensor 130 could be configured to carry out all or a portion of the image processing carried out by the image processing unit 140. In other words, imaging processing could be distributed between the intraoral x-ray imaging sensor 130 and the image processing unit 140. For example, processing hardware could be located in the body of the intraoral x-ray imaging sensor 130 or in the connection 132 connecting the intraoral x-ray imaging sensor 130 to the image processing unit 140.

As described in further detail below, the intraoral x-ray imaging sensor 130 also includes an imaging area that includes a sensor array configured to detect and quantify x-rays at specific "pixel locations" across the imaging area. The intraoral x-ray imaging sensor 130 also includes selector circuitry to selectively couple one or more pixels in a sensor array and to provide an output indicative of the x-rays detected at each specific pixel location to a plurality of readout amplifiers. To improve comfort for the patient and image quality, the size of a non-imaging area of an intraoral x-ray imaging sensor is reduced allowing the overall size of the intraoral x-ray imaging sensor to also be reduced. In some embodiments, as discussed in further detail below, in order to reduce the non-imaging area of the intraoral x-ray imaging sensor, the pixel selector circuitry is incorporated into an imaging area of the intraoral x-ray imaging sensor. However, placing the pixel selector circuitry in the imaging area of the intraoral x-ray imaging sensor may adversely affect the image quality of the dental image by reducing the number of pixels available in the dental image and preventing a complete image from being taken by the intraoral x-ray imaging sensor.

In some implementations, as described in further detail below, the system 110 is configured to use a diagonally arranged pixel selector circuitry positioned in the imaging area of a intraoral x-ray imaging sensor 130 to improve image quality and to provide a more complete image in systems where the pixel selector circuitry is placed in the imaging area of the intraoral x-ray imaging sensor. In some such embodiments, the system 110 is configured to interpolate the pixels that correspond to the diagonally arranged pixel selector circuitry positioned in the imaging area of the intraoral x-ray imaging sensor 130 and generate a dental image that includes the interpolated pixels. In this way, the size of the non-imaging area and the overall size of the intraoral x-ray imaging sensor 130 is reduced, which improves patient comfort, and the image quality of the dental image can be maintained and/or improved.

FIGS. 2-10 are schematic views illustrating different examples of intraoral x-ray imaging sensors 230A-230J (hereinafter, individually "sensor 230A, sensor 230B," etc., or collectively "sensors 230") including a substrate 232 with a non-imaging area 234 and an imaging area 236. The imaging area 236 of substrate 232 includes an array of pixels 238 arranged in rows and columns and a diagonally arranged pixel selector circuitry 240. The non-imaging area 234 of the substrate 232 includes a plurality of readout amplifiers 242 that output signal 250 from sensors 230. In some examples, the non-imaging area 234 of the substrate 232 may also include readout selector circuitry 244 and/or pixel selector circuitry 240. In some examples, the imaging area 236 of the substrate 232 includes readout selector circuitry 244. As described herein, in some examples, the diagonally arranged pixel selector circuitry 240 includes at least one of row selector circuitry or column selector circuitry. As described herein, in some examples, the readout selector circuitry 244 includes row readout selector circuitry with pixel selector circuitry that is column selector circuitry, and in other examples, the readout selector circuitry 244 includes column readout selector circuitry with pixel selector circuitry 240 that is row selector circuitry. Among other advantages, arranging the pixel selector circuitry diagonally allows greater design freedom on where to put the readout amplifiers. For example, the readout amplifiers can be put near any of edges of the sensor.

As described herein, the pixel selector circuitry 240 is described as causing an occlusion in the x-ray image because the pixel selector circuitry 240 may be located on top of the array of pixels 238 in sensors 230. However, it is also understood that the pixel selector circuitry 240 may occupy the same location as some pixels in the array of pixels, thereby replacing the pixel circuitry in those locations in the imaging area. In such examples, the pixel selector circuitry 240 does not cause an occlusion of any specific pixel because there is no collocated sensing pixel at the location occupied by the pixel selector circuitry 240. As such, no individual data value is blocked or "occluded." Instead, it is the image as a whole that is "occluded" due to the sensing pixels that are omitted at areas occupied by the pixel selector circuitry. In summary, although the pixel selector circuitry 240 is described as causing an "occlusion" that can be removed by interpolation of x-ray image data values from non-occluded pixels, it is understood that the "occlusion" may not be an actual occlusion of an individual pixel, but instead a gap in the actual x-ray image data.

In some examples, as illustrated in FIG. 2, the diagonally arranged pixel selector circuitry is diagonally arranged row selector circuitry 240A. In other examples, as illustrated in FIG. 6, the diagonally arranged pixel selector circuitry is diagonally arranged column selector circuitry 240E. In yet other examples, the diagonally arranged pixel selector circuitry 240 may be a combination of diagonally arranged row selector circuitry and column selector circuitry. The substrate 232 of the sensors 230 may be comprised of any suitable material including, but not limited to, silicon. In the examples of FIGS. 2-10, the sensors 230 may be similar or the same as the intraoral x-ray imaging sensor 130 in FIG. 1 and perform similar or the same operations as the intraoral x-ray imaging sensor 130 as described in FIG. 1.

In the illustrated example of FIG. 2, the pixel selector circuitry 240 of sensor 230A diagonally arranged across the imaging area 236 is row selector circuitry 240A. The plurality of readout amplifiers 242 is positioned on one side of the substrate 232 in the non-imaging area 234. For example, as illustrated in FIG. 2, the plurality of readout amplifiers 242 is positioned on the bottom of the substrate 232. In this example, a portion 246 of the plurality of readout amplifiers 242 is diagonally arranged on the bottom of the substrate 232.

The diagonally arranged row selector circuitry 240A of the sensor 230A receives a clock signal that is used to consecutively select each row in the array of pixels 238. In the example of FIG. 2, the selection of the selected row 248 in the array of pixels 238 is indicated by the dotted line shown in the middle of the imaging area 236 of the substrate 232. However, in general, the selection of the selected row 248, in synch with the clock signal, may advance with the clock signal from one side (e.g., the bottom side) of the imaging area 236 and end at the opposite side (e.g., the top side) of the imaging area 236. Optionally, instead of (or in addition to) a clock signal one or more pulse signal(s) may be used to cascade through each row in the array of pixels 238. Based on the clock signal, the selected row 248 in the array of pixels 238 outputs signals to one or more of the plurality of readout amplifiers 242 that are selectively coupled to the pixels in the selected row 248. The one or more of the plurality of readout amplifiers 242 receives the signals from the pixels in the selected row 248 as indicated by the multiple downwards arrows from the dotted line in FIG. 2.

In the example of FIG. 2, the readout selector circuitry is column readout selector circuitry 244A positioned on one edge of the substrate 232. For example, as illustrated in FIG. 2, the column readout selector circuitry 244A is positioned adjacent to the plurality of readout amplifiers 242 on the bottom of the substrate 232. The column readout selector circuitry 244A operates on a clock or pulse that is synchronized with the clock of the row selector circuitry and sequentially causes the output signal from each readout amplifier 242 to generate a serial output signal 250. The column readout selector circuitry 244A sends control signals through column readout select line 280A to control the readout amplifiers 242 to send the pixel signal from each column out of the array as part of the serial output signal 250. In this manner, the value of each pixel in a given row is provided in series to the signal output 250 and, once all of the pixel values in a given row are output, the row selector circuitry 240A moves to the next row in the array.

In the illustrated example of FIG. 3, the pixel selector circuitry positioned diagonally across the imaging area 236 is combined with readout selector circuitry. For example, the row selector circuitry 240B is combined with a portion of the column readout selector circuitry 244B that is located in the imaging area 236 of the substrate 232. Although the combined row selector 240B and column readout selector circuitry 244B are positioned to contact each row in the imaging area, it does not contact all of the columns on the left and right sides of the imaging area. Therefore, additional portions of the column readout selector circuitry 244B are provided in the non-imaging area of the sensor 230B. The plurality of readout amplifiers 242 positioned on the bottom of the substrate 232 receive values from each pixel in a currently activated row from the combined row selector 240B and column readout selector circuitry 244B and from the additional column readout selector circuitry 244B. In this example, a portion 246 of the plurality of readout amplifiers 242 is diagonally arranged on the bottom edge of the substrate 232. The column readout selector circuitry 244B sends control signals through column readout select line 280B to control the readout amplifiers 242 to send the pixel signal from each column out of the array as part of the serial output signal 250.

In the illustrated example of FIG. 4, the pixel selector circuitry arranged diagonally across the imaging area 236 is combined with the readout selector circuitry. For example, the row selector circuitry 240C and column readout selector circuitry 244C are combined to be diagonally arranged in the imaging area 236 in addition to other diagonally arranged portions of the column selector readout circuitry 244C in the imaging area 236. Additionally, the plurality of readout amplifiers 242 is positioned on one side of the substrate in the non-imaging area 234. For example, as illustrated in FIG. 4, the plurality of readout amplifiers 242 is positioned on the bottom of the substrate 232. In this example, a portion 246 of the plurality of readout amplifiers 242 is diagonally arranged on the bottom of the substrate 232. The sensor 230C illustrated in FIG. 4 also includes column readout selector lines 280C to control the column-by-column readout of amplifiers 242.

The diagonally arranged row selector circuitry 240C combined with the column readout selector circuitry 240C of the sensor 230C may perform the same or similar operations as the row selector circuitry and the column readout selector circuitry described above in FIGS. 2 and 3, respectively. For example, the sensor 230C has portions of diagonally arranged column readout selector circuitry 244C in the imaging area 236 of the substrate 232 in addition to the diagonally arranged row selector circuitry 240C and the column readout selector circuitry 244C in the imaging area 236 of the substrate 232. Further, the sensor 230C optionally need not have selector circuitry or readout selector circuitry in the non-imaging area 234 of substrate 232. Accordingly, the non-imaging area 234 of the substrate 232 is reduced to provide space for only the plurality of readout amplifiers 242. In other words, the amount of space required for the non-imaging area 234 of sensor 230C is less than the amount of space required for the non-imaging area 234 of sensors 230A and 230B, thus increasing the size of the imaging area 236 and/or reducing the total size of the sensor 230C for greater patient comfort.

In the illustrated example of FIG. 5, the pixel selector circuitry is combined with readout selector circuitry. For example, the pixel selector circuitry is the row selector circuitry 240D and the readout selector circuitry is column readout selector circuitry 244D. Additionally, the plurality of readout amplifiers 242 may be positioned on one side of the substrate 232 in the non-imaging area 234. For example, as illustrated in FIG. 5, the plurality of readout amplifiers 242 is positioned on the bottom of the substrate 232. In this example, a portion 246 of the plurality of readout amplifiers 242 is diagonally arranged on the bottom of the substrate 232. The sensor 230D illustrated in FIG. 5 also includes column readout selector lines 280D to control the column-by-column readout of amplifiers 242.

The diagonally arranged row selector circuitry 240D combined with the column selector circuitry 244D of the sensor 230D may perform the same or similar operations as the row selector circuitry and the column readout selector circuitry as described above in FIGS. 2-4, respectively. For example, the sensor 230D has pixel selector circuitry including portions of diagonally arranged row selector circuitry 240D in the non-imaging area 234 of the substrate 232 in addition to the row selector circuitry 240D combined with the column readout selector circuitry 244D diagonally arranged in the imaging area 236 of the substrate 232.

In the illustrated example of FIG. 6, the pixel selector circuitry is column selector circuitry 240E. Additionally, the readout selector circuitry is row readout selector circuitry 244E combined with the plurality of readout amplifiers 242 and is positioned on one side of the substrate 232 in the non-imaging area 234. For example, as illustrated in FIG. 6, the combination of the plurality of readout amplifiers 242 and row readout selector circuitry 244E is positioned on the left side of the substrate 232. In this example, a portion 246 of the combination of the plurality of readout amplifiers 242 and row readout selector circuitry 244E is diagonally arranged on the left side of the substrate 232 in the non-imaging area 234. The row readout selector circuitry 244E of the sensor 230E may perform the same or similar operations as the column readout selector circuitry as described in FIGS. 2-5. For example, the row readout selector circuitry 244E operates on a clock or pulse that is synchronized with the clock or pulse of the column selector circuitry 240E and sequentially causes the output signal from each readout amplifier 242 to generate a serial output signal 250. In this manner, the value of each pixel in a given column is provided in series to the signal output 250 and, once all of the pixel values in a given column are output, the column selector circuitry 240E moves to the next column in the array.

The diagonally arranged column selector circuitry 240E of the sensor 230E may receive a clock signal that can be used to consecutively select each column in the array of pixels 238. In the example of FIG. 6, the selection of the selected column 252 is indicated by the dotted line is shown in the middle of the imaging area 236 of the substrate 232. However, in general, the selection of the selected column 252, in synch with the clock signal, may advance from one side (e.g., the left side) of the imaging area 236 and end at the opposite side (e.g., the right side) of the imaging area 236. Based on the clock signal, the selected column 252 in the array of pixels 238 outputs signals to one or more of the plurality of readout amplifiers 242 that are selectively coupled to the pixels in the selected column 252. The one or more of the plurality of readout amplifiers may receive the signals from the pixels in the selected column 252 as indicated by the multiple leftward arrows from the selected column 252.

In the example of FIG. 7, sensor 230F includes a second row readout selector circuitry 274F combined with a second plurality of readout amplifiers 242B positioned on the right side of the substrate 232 in the non-imaging area 234. For example, as illustrated in FIG. 7, the column selector circuitry 240F is diagonally arranged between a first plurality of readout amplifiers 242 and a second plurality of readout amplifiers 242B. The column selector circuitry 240F and the row readout selector circuitry 274F may perform the same or similar operations as the column selector circuitry and the row readout selector circuitry as described above in FIG. 6. However, the column selector circuitry 240F may receive a clock signal that can be used to concurrently select two columns in the array of pixels 238. In other words, instead of consecutively selecting a column 252 as indicated by the dotted line in FIG. 6, the column selector circuitry 250F may concurrently select two columns 252 and 252B as indicated by the two dotted lines in FIG. 7.

Based on the clock signal, the two selected columns 252 and 252B in the array of pixels 238 outputs signals to the first and second plurality of readout amplifiers 242 and 242B that are selectively coupled to the pixels in the two selected columns 252 and 252B. In some embodiments, the clock signal may be two synchronized clock signals. The first and second plurality of readout amplifiers 242 and 242B may receive the signals from the pixels in the two selected columns 252 and 252B as indicated by the multiple leftward and rightward arrows from the two selected columns 252 and 252B to the first and second plurality of readout amplifiers 242 and 242B. After the first and second plurality of readout amplifiers 242 and 242B receive the signals from the two selected column 252 and 252B, the first and second row readout selector circuitries 244F and 274F operate on a clock that is synchronized with the clock of the column selector circuitry 240F and sequentially cause the output signal from each readout amplifier in the first and second pluralities of readout amplifiers 242 and 242B to generate serial output signals 250 and 250B, respectively. In this manner, the value of each pixel in a given column is provided in series to the signal outputs 250 and 250B and, once all of the pixel values in a given column are output, the column selector circuitry 240F moves to the next column(s) in the array.

In the illustrated example of FIG. 8, the pixel selector circuitry is column selector circuitry 240G. Additionally, the readout selector circuitry is the row readout selector circuitry 244G combined with the plurality of readout amplifiers 242 and is positioned on one side of the substrate 232 in the non-imaging area 234. For example, as illustrated in FIG. 8, the row readout selector circuitry 244G combined with the plurality of readout amplifiers 242 is positioned on the left side of the substrate 232. In this example, a portion 246 of the plurality of readout amplifiers 242 is diagonally arranged on the left side of the substrate 232 in the non-imaging area 234.

The column selector circuitry 240G of the sensor 230G may receive a clock signal that can be used to consecutively select each column in the array of pixels 238. For ease of understanding, the selection of the selected column 252 is indicated by the dotted line in FIG. 8 and is shown in the middle of the imaging area 236 of the substrate 232. However, in general, the selection of the selected column 252, in synch with the clock signal, may advance from one side (e.g., the left side) of the imaging area 236 and end at the opposite side (e.g., the right side) of the imaging area 236. Based on the clock signal, the selected column 252 in the array of pixels 238 outputs signals to one or more of the plurality of readout amplifiers 242 that are selectively coupled to the pixels in the selected column 252. In some embodiments, the clock signal may be two synchronized clock signals. The one or more of the plurality of readout amplifiers 242 may receive the signals from the pixels in the selected column 252 as indicated by the multiple leftward arrows from the selected column 252 to the one or more of the plurality of readout amplifiers 242. After the one or more of the plurality of readout amplifiers 242 receives the signals from the selected column 252, the row readout selector circuitry 244G operates on a clock that is synchronized with the clock of the column selector circuitry 240G and sequentially cause the output signal from each readout amplifier in the plurality of readout amplifiers 242 to generate a serial output signal 250. In this manner, the value of each pixel in a given column is provided in series to the signal output 250 and, once all of the pixel values in a given column are output, the column selector circuitry 240G moves to the next column in the array.

In the example of FIG. 9, sensor 230H includes a second row readout selector circuitry 274H combined with a second plurality of readout amplifiers 242B positioned on the right side of the substrate 232 in the non-imaging area 234. For example, as illustrated in FIG. 9, the column selector circuitry 240H is positioned between the first plurality of readout amplifiers 242 on the left side of the substrate 232 and the second plurality of readout amplifiers 242B on the right side of the substrate 232. The column selector circuitry 240H and the row readout selector circuitry 274H may perform the same or similar operations as the column selector circuitry 240G and the row readout selector circuitry as described above in FIG. 8. However, in contrast to the column selector circuitry 240G of FIG. 8, the column selector circuitry 240H may receive a clock signal that can be used to concurrently select two columns 252 and 252B in the array of pixels 238. In other words, instead of consecutively selecting a column 252 as indicated by the dotted line in FIG. 8, the column selector circuitry 240H may concurrently select two columns 252 and 252B as indicated by the two dotted lines in FIG. 9.

Based on the clock signal, the two selected columns 252 and 252B in the array of pixels 238 activate and outputs signals to the first and second plurality of readout amplifiers 242 and 242B that are selectively coupled to the pixels in the two selected columns 252 and 252B. The first and second plurality of readout amplifiers 242 and 242B may receive the signals from the pixels in the two selected columns 252 and 252B as indicated by the multiple leftward and rightward arrows from the two selected columns 252 and 252B to the first and second plurality of readout amplifiers 242 and 242B. After the first and second plurality of readout amplifiers 242 and 242B receive the signals from the two selected column 252 and 252B, the first and second row readout selector circuitries 244H and 274H operate on a clock that is synchronized with the clock of the column selector circuitry 240H and sequentially cause the output signal from each readout amplifier in the first and second pluralities of readout amplifiers 242 and 242B to generate serial output signals 250 and 250B, respectively. In this manner, the value of each pixel in a given column is provided in series to the signal outputs 250 and 250B and, once all of the pixel values in a given column are output, the column selector circuitry 240H moves to the next column in the array.

In the illustrated example of FIG. 10, the pixel selector circuitry is row selector circuitry 240J. In the example of FIG. 10, the readout selector circuitry positioned on one side of the substrate 232 in the non-imaging area 234 is column readout selector circuitry 244J. Additionally, the plurality of readout amplifiers 242 is positioned on one side of the substrate 232 in the non-imaging area 234. For example, as illustrated in FIG. 10, the column readout selector circuitry 244J and the plurality of readout amplifiers 242 are positioned on the bottom of the substrate 232. In this example, a portion 246 of the plurality of readout amplifiers 242 is diagonally arranged on the bottom of the substrate 232.

A portion 254 of the row selector circuitry 240J of the sensor 230J is non-diagonally arranged in the imaging area 236 (e.g., longitudinally arranged) while the rest of the row selector circuitry 240J is diagonally arranged in the imaging area 236 of the substrate 232. The row selector circuitry 240J including portion 254 receives a clock signal that can be used to consecutively select each row of pixels in the array of pixels 238. For ease of understanding, the selection of the selected row 248 as indicated by the dotted line in FIG. 10 is shown in the middle of the imaging area 236 of the substrate 232. However, in general, the selection of the selected row 248, in synch with the clock signal, may advance from one side (e.g., the bottom side) of the imaging area 236 and end at the opposite side (e.g., the top side) of the imaging area 236. Based on the clock signal, the selected row 248 in the array of pixels 238 outputs signals to one or more of the plurality of readout amplifiers 242 that are selectively coupled to the pixels in the selected row 248. The one or more of the plurality of readout amplifiers 242 may receive the signals from the pixels in the selected row 248 as indicated by the multiple downwards arrows from the selected row 248 to the plurality of readout amplifiers 242. After the one or more of the plurality of readout amplifiers 242 receives the signals from the selected row 248, the column readout selector circuitry 244J operates on a clock that is synchronized with the clock of the row selector circuitry 240J and sequentially causes the output signal from each readout amplifier 242 to generate a serial output signal 250. In this manner, the value of each pixel in a given row is provided in series to the signal output 250 and, once all of the pixel values in a given row are output, the row selector circuitry 240J moves to the next row in the array.

Figure 11:
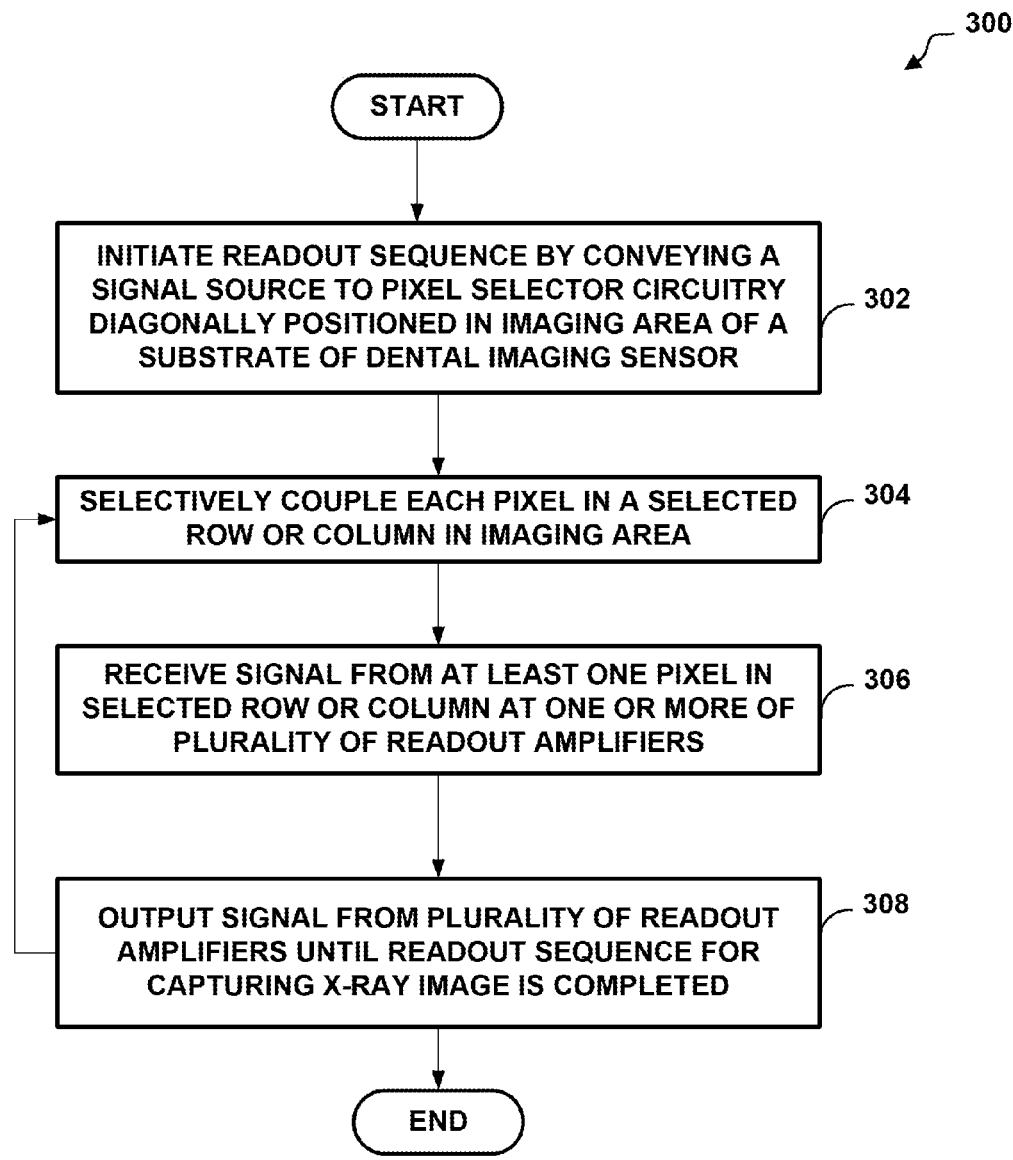
FIG. 11 is a flowchart of a method for capturing an x-ray image with an intraoral x-ray imaging sensor using the dental x-ray system of FIG. 1.

FIG. 11 is a flowchart illustrating a method 300 for capturing an x-ray image with an intraoral x-ray imaging sensor. FIG. 11 is described with respect to sensors 230 as described in FIGS. 2-6, 8, and 10. A readout sequence is initiated by conveying a signal to pixel selector circuitry 240, wherein the pixel selector circuitry 240 is diagonally arranged in an imaging area 236 of a substrate 232 of the intraoral x-ray imaging sensors 230 (block 302). In some embodiments, initiating a readout sequence by conveying a signal to a pixel selector circuitry 240 includes receiving a voltage at an internal or external voltage controlled oscillator (VCO) to the intraoral x-ray imaging sensors 230, and outputting, by the internal or external VCO, the signal source to the pixel selector circuitry 240. In some embodiments, the signal conveyed to the pixel selector circuitry 240 includes a clock signal. In other embodiments, the signal conveyed to the pixel selector circuitry 240 includes a single pulse signal. The signal conveyed to the pixel selector circuitry can originate internally or externally to the circuitry contained in substrate 232. In some embodiments, the pixel selector circuitry includes at least one of a row selector circuitry or a column selector circuitry.

Each pixel in a selected row 248 or selected column 252 of an array of pixels 238 located in the imaging area 236 is selectively coupled by the pixel selector circuitry 240 to a plurality of readout amplifiers 242 (block 304). A signal is received at the plurality of readout amplifiers 242 from at least one pixel in the selected row 248 or selected column 252 indicative of the x-ray detected at the at least one pixel (block 306).

A signal 250 is output from each of the one or more readout amplifiers 242 based on the signal from the at least one pixel until the readout sequence is completed (block 308). In some embodiments, outputting the signal from the one or more of the plurality of readout amplifiers includes outputting a first signal from a first plurality of readout amplifiers, and outputting a second signal from a second plurality of readout amplifiers. Each amplifier is controlled to output its signal by a column readout select line 280 or row readout select line from column or row readout selector circuitry 244.

Figure 12:
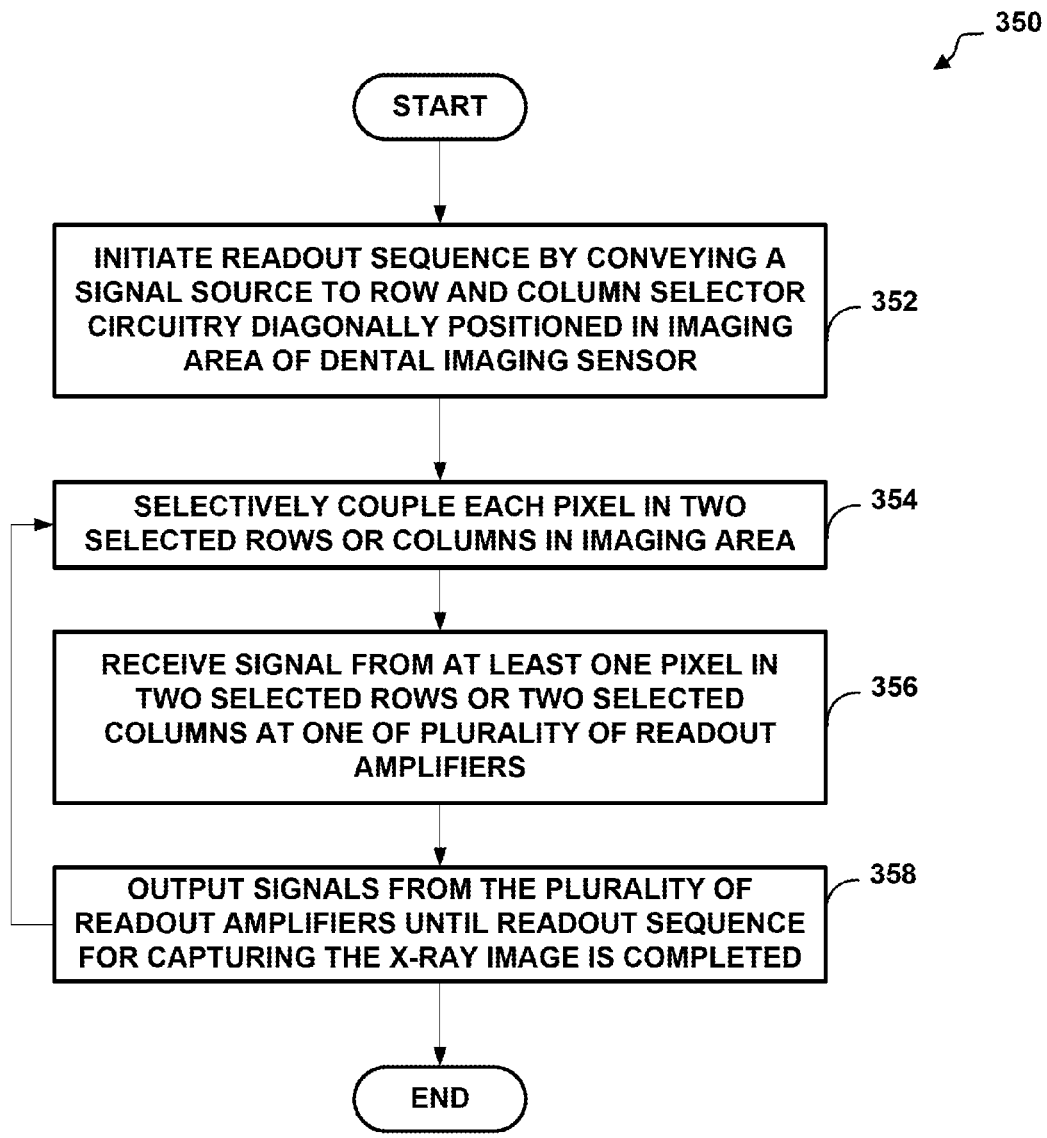
FIG. 12 is a flowchart of a method for capturing an x-ray image with an intraoral x-ray imaging sensor using the dental x-ray system of FIG. 1.

FIG. 12 is a flowchart illustrating another method 350 for capturing an x-ray image with an intraoral x-ray imaging sensor. FIG. 12 is described with respect to sensors 230F and 230H as described in FIGS. 7 and 9, respectively. A readout sequence is initiated by conveying a signal to pixel selector circuitry 240, wherein the pixel selector circuitry 240 is diagonally arranged in an imaging area 236 of a substrate 232 of the intraoral x-ray imaging sensors 230 (block 352). Each pixel in two selected columns 252 and 252B of an array of pixels 238 located in the imaging area 236 is selectively coupled by pixel selector circuitry 240 (block 354) to a plurality of readout amplifiers 242 and 242B. A signal is received at the plurality of readout amplifiers 242 from at least one pixel in the two selected columns 252 and 252B indicative of the x-ray detected at the at least one pixel (block 356).

Signals 250 and 250B are output from the plurality of readout amplifiers 242 based on the signal from the at least one pixel until the readout sequence for capturing the x-ray image is completed (block 358). In some embodiments, the signal 250 is output from a first plurality of readout amplifiers 242 and the signal 250B is output from a second plurality of readout amplifiers 242B. In some embodiments, the pixel selector circuitry 240 includes at least one of a row selector circuitry or a column selector circuitry. Each amplifier is controlled to output its signal by a column readout select line 280 or row readout select line from column or row readout selector circuitry 244.

Figure 13:
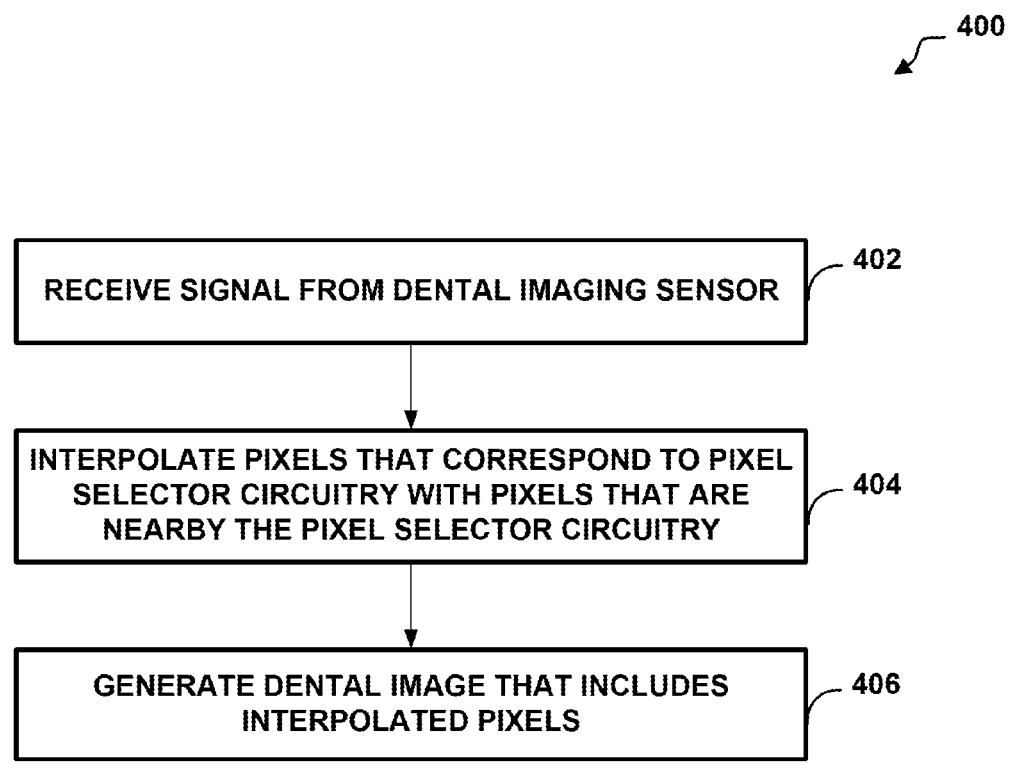
FIG. 13 is a flowchart of a method for operating a dental x-ray system with an intraoral x-ray imaging sensor using the dental x-ray system of FIG. 1.

FIG. 13 is a flowchart illustrating a method 400 for operating a dental x-ray system 110 with an intraoral x-ray imaging sensor 130. FIG. 13 is described with respect to FIG. 1. An image processing unit 140 receives a signal via connection 132 from an intraoral x-ray imaging sensor 130 (block 402). The image processing unit 140 interpolates x-ray image data values for the pixels that correspond to the pixel selector circuitry with pixels that are nearby (e.g., proximate) the pixel selector circuitry (block 404). In some examples, the image processing unit 140 interpolates the pixels that correspond to the pixel selector circuitry with a weighted average of the nearby pixels. In other examples, the image processing unit 140 interpolates the pixels that correspond to the pixel selector circuitry with another function of the nearby pixels. The image processing unit 140 generates a dental image 144 that includes the interpolated pixels (block 406). In some embodiments, the interpolated pixels in the dental image 144 prevent an occlusion of the pixel selector circuitry from forming in the dental image 144. In other words, the dental image 144 provides a complete dental image of the patient 131 without any occlusions from the pixel selector circuitry.

In some embodiments, the image processing unit 140 may generate a test image prior to generating dental image 144 from the signal received from the intraoral x-ray imaging sensor 130. In this way, because x-ray image information is not received for pixels on the imaging sensor surface where the pixel selector circuitry is located, the image processing unit 140 uses the test image to determine the pixels that correspond to placement of a pixel selector circuitry diagonally arranged in the dental image. The image processing unit 140 interpolates x-ray image data values for the pixels that correspond to the placement of the pixel selector circuitry in the dental image with surrounding non-occluded pixels in the dental image. The image processing unit 140 generates a second dental image that includes the interpolated pixels in place of the pixels that correspond to the placement of the pixel selector circuitry in the dental image.

Figure 14A:
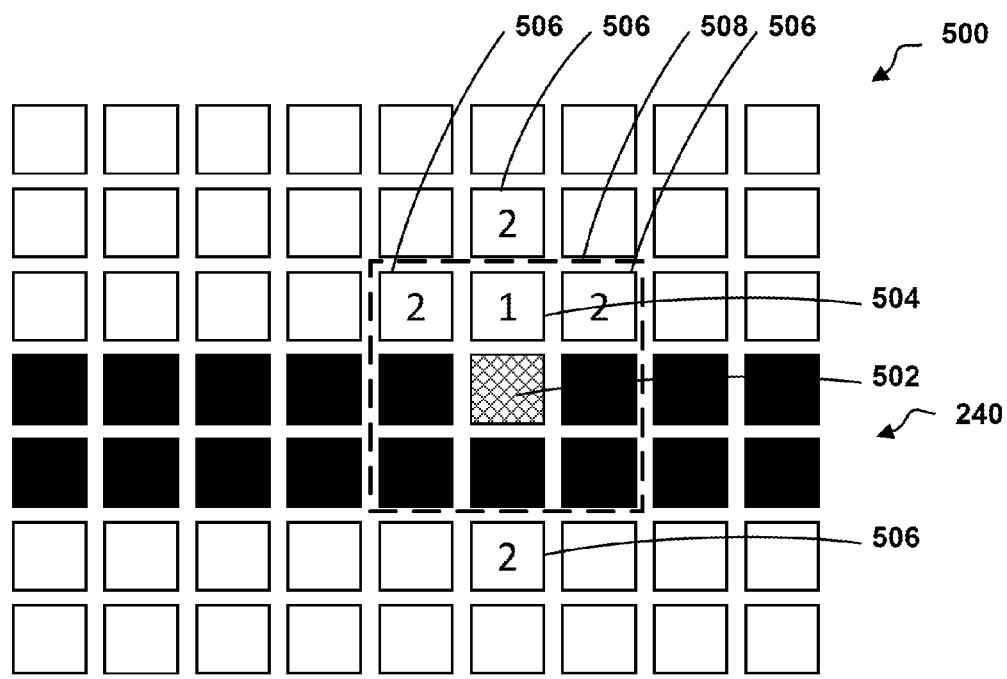
FIG. 14A is a schematic diagram of a two-step pixel interpolation method for an intraoral x-ray imaging sensor with non-diagonally arranged pixel selector circuitry.
Figure 14B:
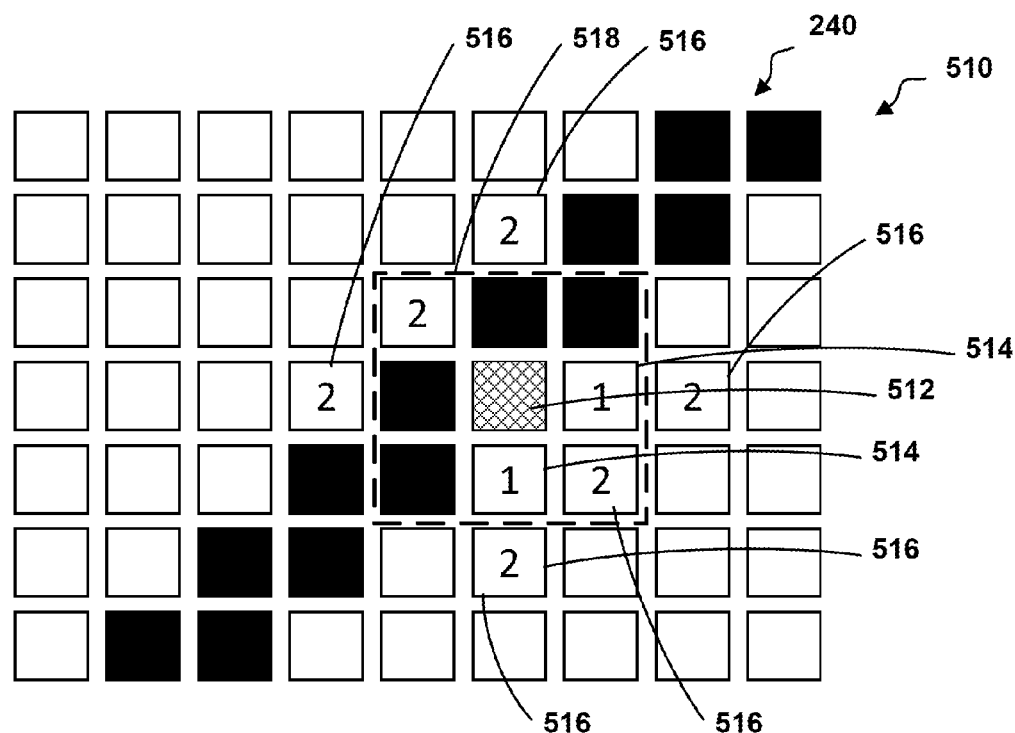
FIG. 14B is a schematic diagram of a two-step pixel interpolation method for an intraoral x-ray imaging sensor with diagonally arranged pixel selector circuitry.

FIGS. 14A and 14B provide examples of two-step pixel interpolation using an intraoral x-ray imaging sensor 500 with a non-diagonally arranged pixel selector circuitry and an intraoral x-ray imaging sensor 510 with a diagonally-arranged pixel selector circuitry, respectively. FIGS. 14A and 14B are described with respect to FIGS. 2-10.

In the example of FIG. 14A, two-step interpolation of sensor 500 includes an target pixel 502, one-step ("1") pixel 504, two-step ("2") pixels 506, and neighboring pixels 508. The target pixel 502 is the pixel of a dental image that has an occlusion (e.g., two rows of occlusion) caused by pixel selector circuitry 240 within the imaging area 236 of sensors 230. For ease of understanding, the target pixel 502 is described in isolation as the pixel to be interpolated; however, the interpolation applied to target pixel 502 may apply to any pixel in the dental image that has an occlusion caused by pixel selector circuitry 240. The one-step pixel 504 is the pixel of the dental image that is one step away from the target pixel 502 and does not have an occlusion caused by the pixel selector circuitry 240 within the imaging area 236 of the sensors 230. The two-step pixels 506 are the pixels of the dental image that are two steps away from the target pixel 502 and also do not have an occlusion caused by the pixel selector circuitry 240 within the imaging area 236 of the sensors 230. The neighboring pixels 508 are the pixels immediately surrounding the target pixel 502 and may have an occlusion caused by the pixel selector circuitry 240 within the imaging area 236 of the sensors 230.

In the illustrated example, the value of the target pixel 502 to be interpolated is replaced by combining the data of the nearby pixels that do not have an occlusion caused by the pixel selector circuitry 240 within the imaging area 236 of the sensors 230. For example, as illustrated in FIG. 14A, one one-step pixel 504 and four two-step pixels 506 for a total of five non-occluded pixels can be used for interpolation of the target pixel 502.

In the example of FIG. 14B, two-step interpolation of sensor 510 includes a target pixel 512 to be interpolated, one-step pixels 514, two-step pixels 516, and neighboring pixels 518. The target pixel 512 to be interpolated is the pixel of a dental image that has an occlusion (e.g., two rows of occlusion) caused by pixel selector circuitry 240 within the imaging area 236 of sensors 230. The one-step pixels 514 are the pixels of the dental image that are one step away from the target pixel 512 and do not have an occlusion caused by the pixel selector circuitry 240 within the imaging area 236 of the sensors 230. The two-step pixels 516 are the pixels of the dental image that are two steps away from the target pixel 512 and do not have an occlusion caused by the pixel selector circuitry 240 within the imaging area 236 of the sensors 230. The neighboring pixels 518 are the pixels immediately surrounding the target pixel 512 to be interpolated and may have an occlusion caused by the pixel selector circuitry 240 within the imaging area 236 of the sensors 230.

In the illustrated example, the target pixel 512 may be replaced by combining (i.e., interpolating) the data of the nearby pixels that do not have an occlusion caused by the pixel selector circuitry 240 within the imaging area 236 of the sensors 230. For example, as illustrated in FIG. 14B, two one-step pixels 514 and six two-step pixels 516 for a total of eight non-occluded pixels can be used for interpolation of the target pixel 512. In contrast with FIG. 14A, eight non-occluded pixels provide more data for interpolation than five non-occluded pixels of FIG. 14A. Accordingly, the two-step interpolation of sensor 510 will provide a higher quality image than the two-step interpolation of sensor 500 because additional data is available to be included in the interpolation of the target pixel 502.

Although, FIGS. 14A and 14B are described and illustrated as implementing two-step interpolation of pixel selector circuitry 240 that is two pixels wide, it is understood that FIGS. 14A and 14B each describe and illustrate an example of many possible examples. For example, any suitable interpolation technique may be used instead of two-step interpolation including one-step interpolation, or more than two-step interpolation. Additionally, the pixel selector circuitry can be narrower or wider than two pixels.

Figure 15A:
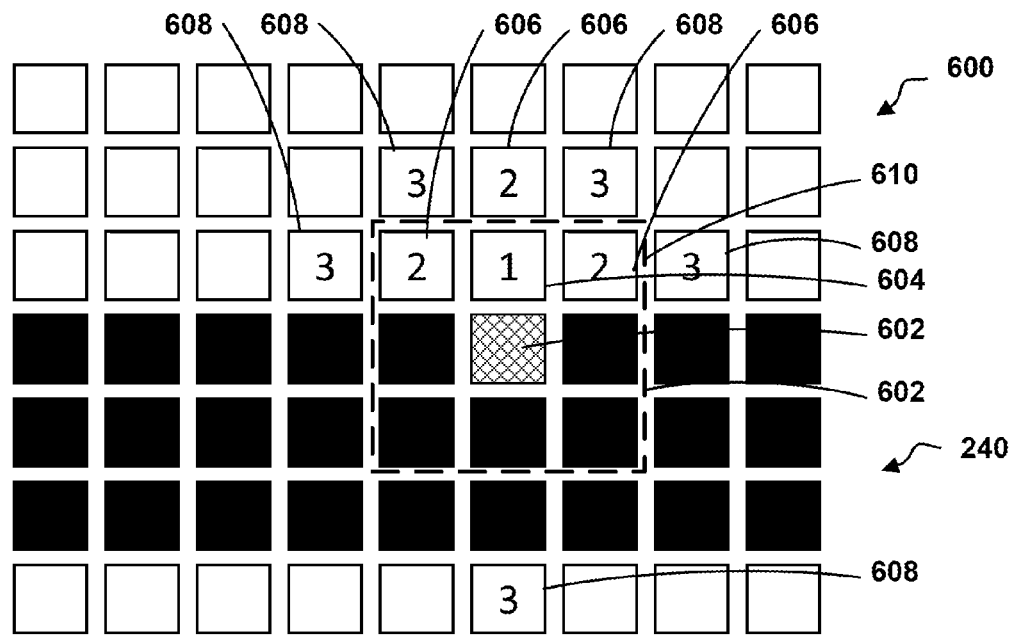
FIG. 15A is a block diagram of a three-step pixel interpolation method for an intraoral x-ray imaging sensor with non-diagonally arranged pixel selector circuitry.
Figure 15B:
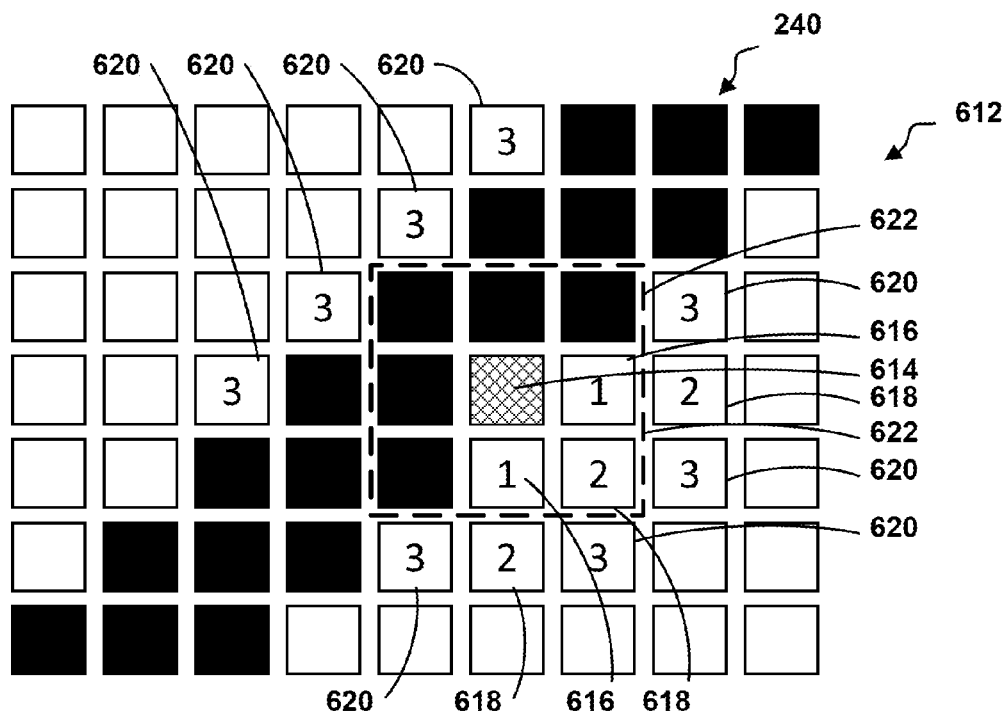
FIG. 15B is a block diagram of a three-step pixel interpolation method for an intraoral x-ray imaging sensor with diagonally arranged pixel selector circuitry.

FIGS. 15A and 15B are block diagrams illustrating a comparison of three-step pixel interpolation between an intraoral x-ray imaging sensor 600 with a non-diagonally arranged pixel selector circuitry versus an intraoral x-ray imaging sensor 612 with a diagonally arranged pixel selector circuitry, according to one embodiment of the invention. FIGS. 15A and 15B are described with respect to FIGS. 2-10.

In the example of FIG. 15A, three-step interpolation of sensor 600 includes a target pixel 602 to be interpolated, one-step pixel 604, two-step pixels 606, three-step pixels 608, and neighboring pixels 610. The target pixel 602 to be interpolated is the pixel of a dental image that has an occlusion (e.g., three rows of occlusion) caused by pixel selector circuitry 240 within the imaging area 236 of sensors 230. For ease of understanding, the target pixel 602 to be interpolated is described in isolation; however, the interpolation applied to target pixel 602 may apply to any pixel in the dental image that has an occlusion caused by pixel selector circuitry 240. The one-step ("1") pixel 604 is the pixel of the dental image that is one step away from the target pixel 602 and does not have an occlusion caused by the pixel selector circuitry 240 within the imaging area 236 of the sensors 230. The two-step ("2") pixels 606 are the pixels of the dental image that are two steps away from the target pixel 602 and do not have an occlusion caused by the pixel selector circuitry 240 within the imaging area 236 of the sensors 230. The three-step ("3") pixels 608 are the pixels of the dental image that are three steps away from the target pixel 602 and do not have an occlusion caused by the pixel selector circuitry 240 within the imaging area 236 of the sensors 230. The neighboring pixels 610 are the pixels immediately surrounding the target pixel 602 and may have an occlusion caused by the pixel selector circuitry 240 within the imaging area 236 of the sensors 230.

In the illustrated example, the target pixel 602 may be replaced by combining the data of the nearby pixels that do not have an occlusion caused by the pixel selector circuitry 240 within the imaging area 236 of the sensors 230. For example, as illustrated in FIG. 15A, one one-step pixel 604, three two-step pixels 606, and five three-step pixels 608 for a total of nine non-occluded pixels can be used for the interpolation of the target pixel 602.

In the example of FIG. 15B, three-step interpolation of sensor 612 includes a target pixel 614, one-step pixels 616, two-step pixels 618, three-step pixels 620, and neighboring pixels 622. The target pixel 614 to be interpolated is the pixel of a dental image that has an occlusion (e.g., three rows of occlusion) caused by pixel selector circuitry 240 within the imaging area 236 of sensors 230. The one-step ("1") pixels 616 are the pixels of the dental image that are one step away from the target pixel 614 and do not have an occlusion caused by the pixel selector circuitry 240 within the imaging area 236 of the sensors 230. The two-step ("2") pixels 618 are the pixels of the dental image that are two steps away from the target pixel 614 and do not have an occlusion caused by the pixel selector circuitry 240 within the imaging area 236 of the sensors 230. The three-step ("3") pixels 620 are the pixels of the dental image that are three steps away from the target pixel 614 and do not have an occlusion caused by the pixel selector circuitry 240 within the imaging area 236 of the sensors 230. The neighboring pixels 622 are the pixels immediately surrounding the target pixel 614 and may have an occlusion caused by the pixel selector circuitry 240 within the imaging area 236 of the sensors 230.

In the illustrated example, the target pixel 614 is interpolated by combining the data of nearby pixels that do not have an occlusion caused by the pixel selector circuitry 240 within the imaging area 236 of the sensors 230. For example, as illustrated in FIG. 15B, two one-step pixels 616, three two-step pixels 618, and eight three-step pixels 620 for a total of thirteen non-occluded pixels can be used for the interpolation of the target pixel 614. In contrast with FIG. 15A, thirteen non-occluded pixels provide more data for interpolation than nine non-occluded pixels of FIG. 15A. Accordingly, the three-step interpolation of sensor 612 will provide a higher quality image than the three-step interpolation of sensor 600 because additional data is available to be included in the interpolation of the target pixel 614.

Although, FIGS. 15A and 15B are described and illustrated as implementing three-step interpolation of pixel selector circuitry 240 that is three pixels wide, it is understood that FIGS. 15A and 15B each describe and illustrate an example of many possible examples. For example, any suitable interpolation technique may be used instead of three-step interpolation including one-step interpolation, two-step interpolation, or more than three-step interpolation. In other words, there is not necessarily any particular limit to how many steps away a pixel can be from the target pixel 502 or 512 and still be used for the interpolation. Additionally, the pixel selector circuitry 240 can be narrower or wider. It is understood that different interpolation methods can be applied to different pixels within the same image.

Figure 16:
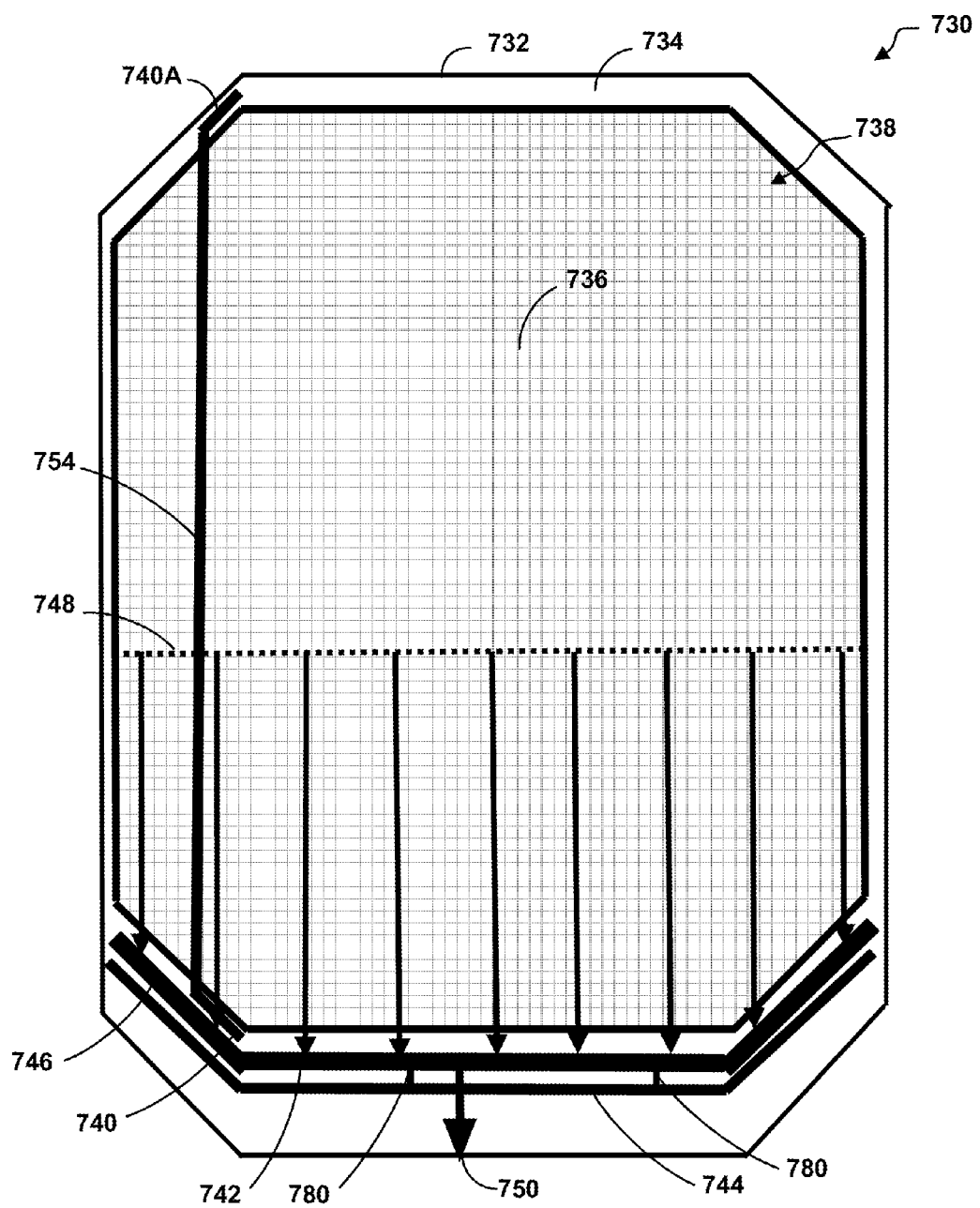
FIG. 16 is a schematic view of an example of an intraoral x-ray imaging sensor including an imaging area and a non-imaging area with a diagonally arranged pixel selector circuitry for use in the dental x-ray system of FIG. 1.

FIG. 16 is a schematic view of an example of an intraoral x-ray imaging sensor 730 including an imaging area 736 and a non-imaging area 734 with diagonally arranged pixel selector circuitry 740 for use in the dental x-ray system of FIG. 1. The imaging area 736 of substrate 732 includes an array of pixels 738 arranged in rows and columns and a diagonally arranged pixel selector circuitry 740. The non-imaging area 734 of the substrate 732 includes a plurality of readout amplifiers 742 that output signal 750 from sensor 730.

In the illustrated example of FIG. 16, the pixel selector circuitry 740 is row selector circuitry 740A. In the example of FIG. 16, the readout selector circuitry 744 positioned on one side of the substrate 732 in the non-imaging area 734 is column readout selector circuitry 744A. Additionally, the plurality of readout amplifiers 742 is positioned on one side of the substrate 732 in the non-imaging area 734. For example, as illustrated in FIG. 16, the column readout selector circuitry 744A and the plurality of readout amplifiers 742 are positioned on the bottom of the substrate 732. In this example, a portion 746 of the plurality of readout amplifiers 742 is diagonally arranged on the bottom of the substrate 732. The sensor 730 illustrated in FIG. 16 also includes column readout selector lines 780 to control the column-by-column readout of amplifiers 742.

A portion 754 of the row selector circuitry 740A of the sensor 730 is non-diagonally arranged in the imaging area 236 (e.g., longitudinally arranged) while the rest of the row selector circuitry 740A is diagonally arranged in the non-imaging area 734 of the substrate 732. For example, as illustrated in FIG. 16, the remaining portions of row selector circuitry 740A other than portion 754 are diagonally arranged in the non-imaging area 734 of the substrate 732 and located near and align with the chamfered corners of substrate 732. In this manner, the location and alignment of the remaining portions of the row selector circuitry 740A allows for the substrate 732 to be reduced in size when compared to a substrate that has remaining portions of row selector circuitry 740A positioned away from and not aligned with the chamfered corners of the substrate 732.

The row selector circuitry 740A receives a clock signal that can be used to consecutively select each row of pixels in the array of pixels 738. For ease of understanding, the selection of the selected row 748 as indicated by the dotted line in FIG. 16 is shown in the middle of the imaging area 736 of the substrate 732. However, in general, the selection of the selected row 748, in synch with the clock signal, may advance from one side (e.g., the bottom side) of the imaging area 736 and end at the opposite side (e.g., the top side) of the imaging area 736. Based on the clock signal, the selected row 748 in the array of pixels 738 outputs signals to one or more of the plurality of readout amplifiers 742 that are selectively coupled to the pixels in the selected row 748. The one or more of the plurality of readout amplifiers 742 that are selectively coupled to the pixels in the selected row 748 may receive the signals from the pixels in the selected row 748 as indicated by the multiple downwards arrows from the selected row 748 to the plurality of readout amplifiers 742. After the one or more of the plurality of readout amplifiers 742 receives the signals from the selected row 748, the column readout selector circuitry 744A operates on a clock that is synchronized with the clock of the row selector circuitry 740A and sequentially sends control signals through column readout selector lines 780 to control each readout amplifier 742 to generate a serial output signal 750. In this manner, the value of each pixel in a given row is provided in series to the signal output 750 and, once all of the pixel values in a given row are output, the row selector circuitry 740A moves to the next row in the array. This operation continues until the readout sequence of all the rows in the array of pixels 738 has been completed.

As described herein, the pixel selector circuitry 740 is described as causing an occlusion in the x-ray image because the pixel selector circuitry 740 may be located on top of the array of pixels 738 in sensor 730. However, it is also understood that the pixel selector circuitry 740 may occupy the same location as some pixels in the array of pixels, thereby replacing the pixel circuitry in those locations in the imaging area. In such examples, the pixel selector circuitry 740 does not cause an occlusion of any specific pixel because there is no collocated sensing pixel at the location occupied by the pixel selector circuitry 740. As such, no individual data value is blocked or "occluded." Instead, it is the image as a whole that is "occluded" due to the sensing pixels that are omitted at areas occupied by the pixel selector circuitry. In summary, although the pixel selector circuitry 740 is described as causing an "occlusion" that can be removed by interpolation of x-ray image data values from non-occluded pixels, it is understood that the "occlusion" may not be an actual occlusion of an individual pixel, but instead a gap in the actual x-ray image data.

Thus, the invention provides, among other things, devices, methods, and systems for generating a dental image with interpolated pixels from an intraoral x-ray imaging sensor having a diagonally arranged pixel selector circuitry in an imaging area or a non-imaging area of the intraoral x-ray imaging sensor. Various features and advantages of the invention are set forth in the following claims.

What is claimed is:
1. An intraoral x-ray imaging sensor comprising:
 a substrate having an imaging area and a non-imaging area;
 a plurality of readout amplifiers located in the non-imaging area of the substrate;
 an array of pixels located on the imaging area of the substrate and arranged as a plurality of rows and columns, wherein each pixel of the array of pixels is selectively coupled to one or more of the plurality of readout amplifiers; and
 pixel selector circuitry diagonally arranged in the imaging area of the substrate.

2. The intraoral x-ray imaging sensor of claim 1, wherein the pixel selector circuitry includes row selector circuitry.

3. The intraoral x-ray imaging sensor of claim 2, further comprising column readout selector circuitry.

4. The intraoral x-ray imaging sensor of claim 1, wherein the pixel selector circuitry includes column selector circuitry.

5. The intraoral x-ray imaging sensor of claim 4, further comprising row readout selector circuitry.

6. The intraoral x-ray imaging sensor of claim 1, wherein a portion of the plurality of readout amplifiers is diagonally arranged in the non-imaging area of the substrate.

7. The intraoral x-ray imaging sensor of claim 6, wherein the plurality of readout amplifiers includes a first plurality of readout amplifiers and a second plurality of readout amplifiers, wherein the first plurality of readout amplifiers is positioned on a first side of the substrate between a first edge of the imaging area and a first edge of the substrate, and wherein the second plurality of readout amplifiers is positioned on a second side opposite the first side between a second edge of the imaging area and a second edge of the substrate.

8. The intraoral x-ray imaging sensor of claim 1, wherein the pixel selector circuitry diagonally arranged in the imaging area of the substrate includes a portion of a column selector circuitry diagonally arranged in the imaging area of the substrate.

9. The intraoral x-ray imaging sensor of claim 1, wherein the pixel selector circuitry further includes one or more portions of a row selector circuitry or one or more portions of a column selector circuitry diagonally arranged in the non-imaging area of the substrate.

10. The intraoral x-ray imaging sensor of claim 1, wherein the arrangement of the pixel selector circuitry in the imaging area of the substrate causes an occlusion in the imaging area of the substrate.

11. The intraoral x-ray imaging sensor of claim 10, further comprising a controller configured to mitigate the occlusion by interpolating data values of proximally located and non-occluded pixels.

12. The intraoral x-ray imaging sensor of claim 11, wherein the interpolation of the data values in the proximally located and non-occluded pixels includes one or more steps of interpolation.

13. A method of capturing an x-ray image with an intraoral x-ray imaging sensor, the method comprising:
   initiating a readout sequence by conveying a signal to pixel selector circuitry, wherein the pixel selector circuitry is diagonally arranged in an imaging area of a substrate of the intraoral x-ray imaging sensor;
   selectively coupling each pixel in a selected row or selected column of an array of pixels located in the imaging area to one or more of a plurality of readout amplifiers;
   receiving, at the one or more of a plurality of readout amplifiers, a signal from at least one pixel in the selected row or selected column; and
   outputting a signal from the one or more of the plurality of readout amplifiers based on the signal from the at least one pixel until the readout sequence for capturing the x-ray image is completed.

14. The method of claim 13, wherein initiating the readout sequence by conveying the signal source to the pixel selector circuitry comprises outputting, by a signal source, the signal to the pixel selector circuitry.

15. The method of claim 13, wherein selectively coupling each pixel in the selected row or selected column of the array of pixels located in the imaging area to the one or more of the plurality of readout amplifiers comprises selectively coupling each pixel in two selected rows or two selected columns of the array of pixels located in the imaging area to the one or more of the plurality of readout amplifiers.

16. The method of claim 15, wherein receiving the signal from the at least one pixel in the selected row or selected column comprises receiving the signal from at least one pixel in the two selected rows or the two selected columns.

17. The method of claim 16, wherein outputting the signal from the one or more of the plurality of readout amplifiers includes
   outputting a first signal from a first plurality of readout amplifiers; and
   outputting a second signal from a second plurality of readout amplifiers.

18. The method of claim 13, wherein the pixel selector circuitry includes at least one selected from the group consisting of row selector circuitry or column selector circuitry.

19. The method of claim 13, further comprising mitigating occlusion caused by the positioning of the pixel selector circuitry in the imaging area of the substrate by interpolating data values in proximally located and non-occluded pixels.

20. The method of claim 19, wherein the interpolation of the data values in the proximally located and non-occluded pixels includes one or more steps of interpolation.

21. A dental x-ray system comprising:
   an intraoral x-ray imaging sensor having
      a substrate having an imaging area and a non-imaging area;
      a plurality of readout amplifiers located in the non-imaging area of the substrate;
      an array of pixels located in the imaging area of the substrate and arranged as a plurality of rows and columns, wherein each pixel of the array of pixels is selectively coupled to one or more of the plurality of readout amplifiers; and
      pixel selector circuitry diagonally arranged in the imaging area of the substrate; and
   a dental image generation device having
      memory; and
      one or more processors configured to
         receive signals from the intraoral x-ray imaging sensor,
         interpolate pixels that correspond to the pixel selector circuitry with pixels that are near the pixel selector circuitry,
         generate a dental image that includes the interpolated pixels, and
         store the dental image in the memory.

22. A method for operating a dental x-ray system, the method comprising:
   receiving signals from an intraoral x-ray imaging sensor containing pixel selector circuitry diagonally arranged in an imaging area of a substrate;
   interpolating values of pixels that correspond to locations of the pixel selector circuitry using values of pixels that are near the pixel selector circuitry; and
   generating a dental image that includes the interpolated pixel values.

23. An intraoral x-ray imaging sensor comprising:
   a substrate having an imaging area and a non-imaging area;
   a plurality of readout amplifiers located in the non-imaging area of the substrate;
   an array of pixels located on the imaging area of the substrate and arranged as a plurality of rows and columns, wherein each pixel of the array of pixels is selectively coupled to one or more of the plurality of readout amplifiers; and
   pixel selector circuitry diagonally arranged in the non-imaging area of the substrate.

* * * * *